United States Patent [19]

Stuart

[11] Patent Number: 4,800,905
[45] Date of Patent: Jan. 31, 1989

[54] SEMI-RIGID TOOTHPICK WITH PROTECTIVE CASE HANDLE

[76] Inventor: Dennis D. Stuart, P.O. Box 657, Woodacre, Calif. 94973

[21] Appl. No.: 88,367

[22] Filed: Aug. 21, 1987

Related U.S. Application Data

[63] Continuation-in-part of Ser. No. 898,563, Aug. 21, 1986, abandoned.

[51] Int. Cl.[4] ............................................. A61C 15/00
[52] U.S. Cl. ..................................... 132/328; 132/321
[58] Field of Search ................... 132/89, 90, 91, 92 R, 132/92 A, 93; D28/64

[56] References Cited

U.S. PATENT DOCUMENTS

| | | | |
|---|---|---|---|
| 186,952 | 2/1877 | Poznanski | 132/90 |
| 516,409 | 3/1894 | Southwell | 132/89 |
| 740,586 | 10/1903 | Ohlsson | 132/90 |
| 1,355,037 | 10/1920 | Dziuk | 132/90 |
| 1,527,028 | 2/1925 | Daniel | 132/89 |
| 2,931,371 | 4/1960 | Petitta | 132/89 |
| 3,295,207 | 1/1967 | Leonard | 433/126 |
| 3,954,115 | 5/1976 | Bengtsson | 132/89 |
| 3,999,562 | 12/1976 | Reukauf | 132/89 |
| 4,040,433 | 8/1977 | Edison | 132/89 |
| 4,364,730 | 12/1982 | Axelsson | 433/72 |

FOREIGN PATENT DOCUMENTS 0191896  1/1923  United Kingdom ................. 132/89

*Primary Examiner*—Gene Mancene
*Assistant Examiner*—Adriene J. Lepiane
*Attorney, Agent, or Firm*—Townsend and Townsend

[57] ABSTRACT

A reusable toothpick is mounted to a double ended bayonet mount. The bayonet mount is unoccupied at one end and has the toothpick grasped medially at the opposite end. The double ended bayonet mount is in turn received into a handle having a hollow cavity for receiving the full working length of the toothpick as it protrudes from one of the bayonet mounts. In a first position of the bayonet mount with respect to the handle, the toothpick is fitted within the handle, and the handle closed by the bayonet mount so as to provide a sanitary and safe toothpick transport. In a second and reverse position of the bayonet mount, the toothpick is mounted for manipulation from the handle and sufficient overall length of the handle is imparted to the toothpick which, in addition to the design features of the pick itself (appropriate narrowness, semi-blunted tip, semi-rigid composition, 90° bendability and fixation, and incremental millimeter markings), allow for convenient use by the user in the removal of plaque and food debris from all interproximal and subgingival areas of the oral cavity. The handle is elliptical in section so that the flat handle sides parallel to the major axis of the elliptical section can be grasped between the fingers. The attached toothpick is elliptical in section with the major axis at approximate right angles to the major axis of the handle. This design permits bending of the toothpick in the plane of the handle and manipulation of the toothpick from the handle to clean the gingival sulcuf of the teeth.

4 Claims, 4 Drawing Sheets

U.S. Patent  Jan. 31, 1989  Sheet 1 of 4  4,800,905
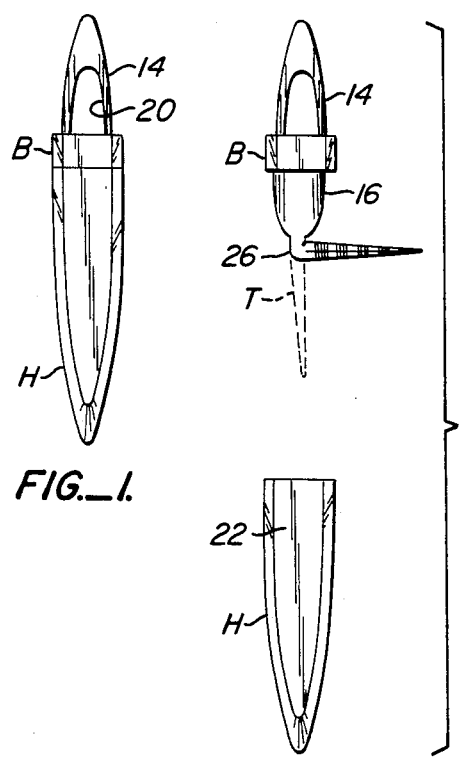
FIG._1.
FIG._2.
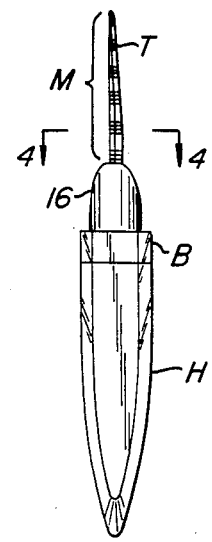
FIG._3.
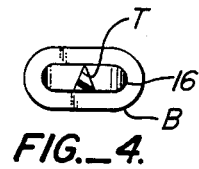
FIG._4.
FIG._5.

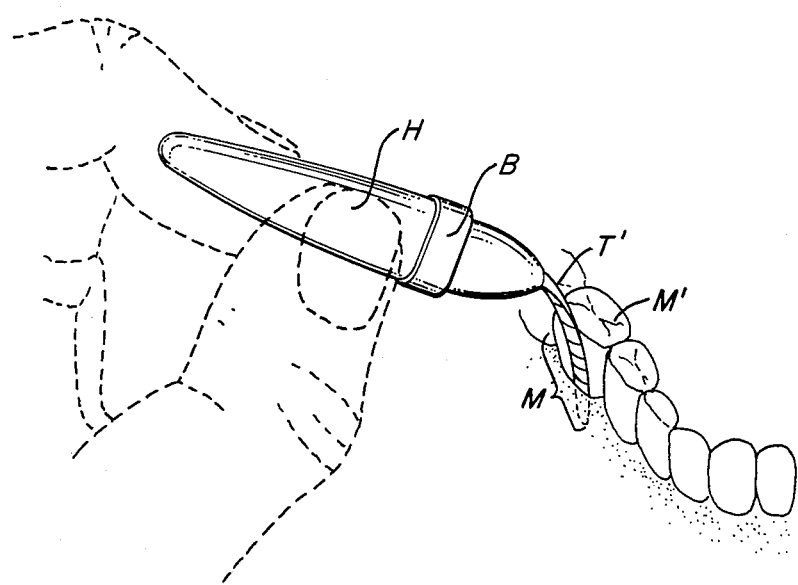
FIG._6.
FIG._7.

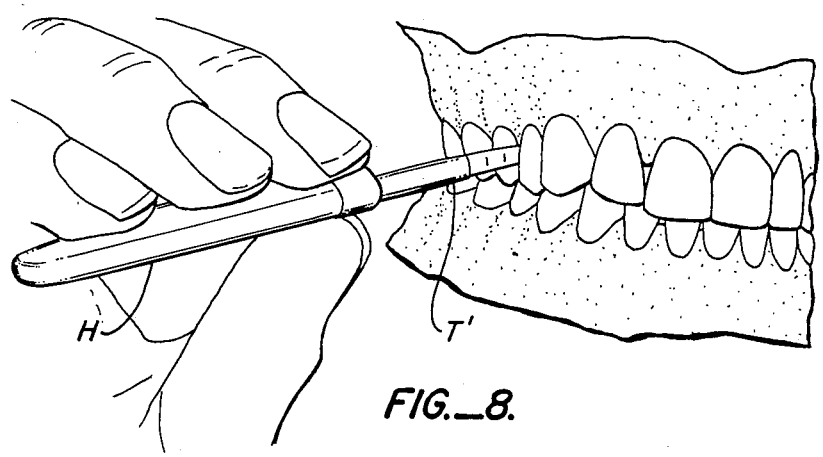
FIG._8.
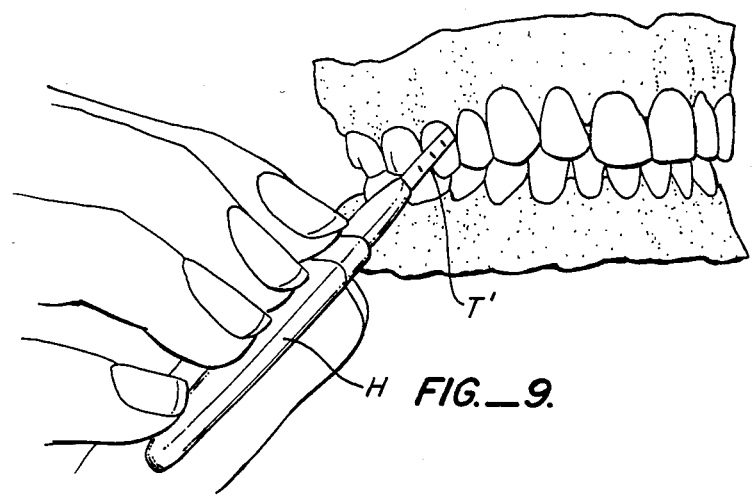
FIG._9.
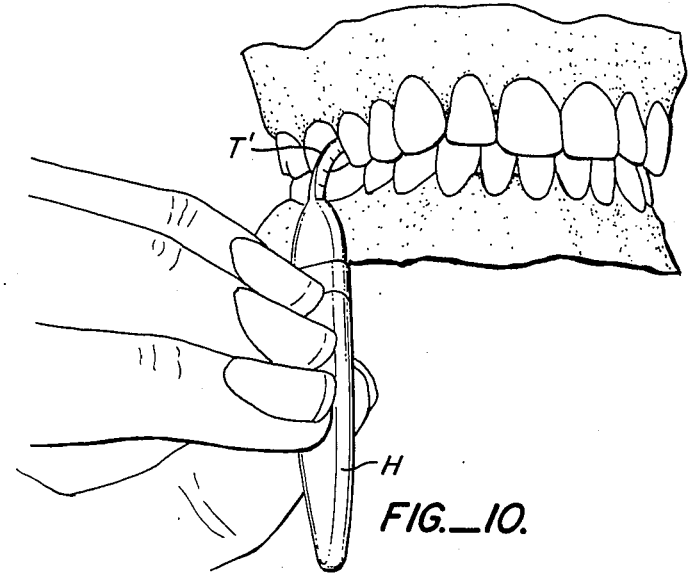
FIG._10.

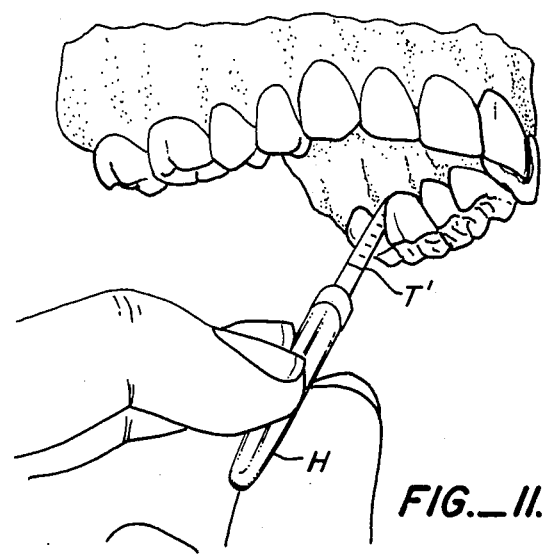
FIG._11.
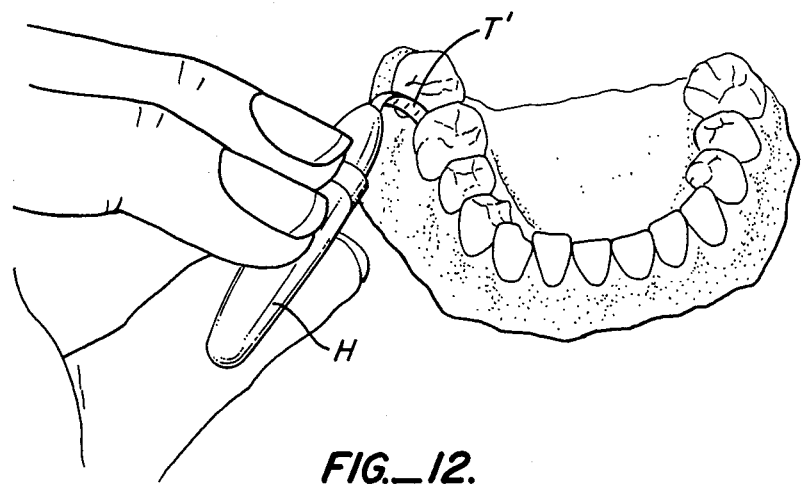
FIG._12.

SEMI-RIGID TOOTHPICK WITH PROTECTIVE CASE HANDLE

This application is a continuation-in-part of copending patent application Ser. No. 898,563 filed Aug. 21, 1986, abandoned Dec. 15, 1987.

BACKGROUND OF THE INVENTION

This invention relates to toothpicks. More particularly it relates to a toothpick mounted to a case handle.

DESCRIPTION OF THE PRIOR ART

Toothpicks are beneficial dental devices. Unfortunately, they do not enjoy deserved use because they are a danger to carry. For example, when they are carried unprotected in the pocket, they become dirty and are not sanitary. Moreover, they frequently end up impaled into the carrying person.

Furthermore, toothpicks have historically not been properly designed to fulfill the criteria of optimal oral hygiene: They are not of sufficient overall length and no considerations have been given in regards to the mechanical demands of the handle in relationship to the pick (the ratio of the handle to the pick must be approximately three (3) times for proper leverage); also, they have not allowed for bending of the pick portion at 90° (and kept at 90°) to the handle for proper interproximal and subgingival access to the posterior teeth. Without such aforementioned mechanical design features, "prior art" toothpicks have comprised function.

It is known to enclose toothpicks in protective sanitary containers. See Edison U.S. Pat. No. 4,040,433. While this may solve the problem of hygiene and protection of the user from impalement, it does not provide for suitable manipulation of the toothpick or suitable length for necessary cleaning and treatment of molars, especially in cleaning the gingival sulcuf (area of the tooth below the gum but not attached to the flesh) of the human dentition.

SUMMARY OF THE INVENTION

A reusable toothpick is mounted to a double ended bayonet mount. The bayonet mount is unoccupied at one end and has the toothpick grasped medially at the opposite end. The double ended bayonet mount is in turn received into a handle having a hollow cavity for receiving the full working length of the toothpick as it protrudes from one of the bayonet mounts. In a first position of the bayonet mount with respect to the handle, the toothpick is fitted within the handle, and the handle closed by the bayonet mount so as to provide a sanitary and safe toothpick transport. In a second and reverse position of the bayonet mount, the toothpick is mounted for manipulation from the handle and given sufficient hand retention to provide leverage when manipulating the toothpick. Sufficient overall length is imparted to the toothpick by the handle and along with its right angle configurability it may be conveniently used in all interproximal and subgingival areas of the oral cavity.

The handle is elliptical in section so that the flat handle sides parallel to the major axis of the elliptical section can be grasped between the fingers. The attached toothpick is elliptical in section with the major axis at approximate right angles to the major axis of the handle. This design permits bending of the toothpick in the plane of the handle and manipulation of the toothpick from the handle to clean the gingival sulcuf of the teeth.

BRIEF DESCRIPTION OF THE DRAWINGS

Other objects, features and advantages of the invention will become more apparent after referring to the following specification in which:

FIG. 1 is a side elevation of the toothpick handle illustrating the handle encasing one end of the bayonet mounted toothpick;

FIG. 2 is a picture illustrating the toothpick withdrawn from the handle;

FIG. 3 is a side elevation similar to FIG. 1 illustrating the toothpick mounted to the handle;

FIG. 4 is an end elevation section along lines 4—4 of FIG. 3 illustrating the toothpick profile;

FIG. 5 is a perspective of a user manipulating the toothpick of FIG. 3 illustrating the retention and leverage provided.

FIG. 6 is an end view with the projecting toothpick extending toward the viewer illustrating the elliptically sectioned handle with it projecting elliptically shaped toothpick, it being noted that the major axis of the elliptically shaped handle is at right angles to the major axis of the elliptically shaped toothpick; and, FIG. 7 is a view with the toothpick held by fingers shown in phantom with the bent toothpick being manipulated subgingivally to clean a periodontal pocket, here the gingival sulcuf of a molar.

FIG. 8 is a perspective of the pick being utilized perpendicular to the longitudinal axis of the teeth;

FIG. 9 is a perspective of the pick being used at 45° to the teeth, it being apparent that variations of this angle are covered as well;

FIG. 10 is a perspective of the pick being used to access the distal portion of the teeth;

FIG. 11 is a perspective of the pick being used to access the teeth from the palatal or lingual direction; and, FIG. 12 is a perspective of the pick being used to access the distal surface from the facial aspect at the first molar.

It is an object of this invention to disclose a relationship between the section of the handle for manipulating the toothpick and the section of the toothpick itself as mounted to the handle to enable bending and subgingival penetration of the pick with resultant cleaning of the dentition. The handle is flattened with preferably an elliptical cross section so that the flatten sides of the handle may be grasped between the fingers. The toothpick is also given a flattened cross section which is preferably elliptical. However, this cross section is flattened at right angles to the cross section of the handle. This relationship enables the toothpick to be bent in the plane of the flattened section of the handle.

An advantage of the capability of bending the toothpick in the plane of the handle is that optimum manipulation of the toothpick for cleaning the periodontal pockets can occur. For example, the pick can conveniently be used for the cleaning of the gingival sulcuf of the teeth where required.

BRIEF DESCRIPTION OF THE PREFERRED EMBODIMENTS

Referring to FIG. 1, the encased toothpick according to this invention is illustrated. Specifically, bayonet fitting B is shown placed within the handle H. An attached toothpick T (see FIG. 2) is disposed wholly within handle H. Bayonet mount 14 protrudes from the upper end of the bayonet fitting B. It is provided with an aperture 20 which will enable mounting to a retention device such as a keychain and simultaneously provide bayonet mount 14 with flexibility once received interior of handle H.

Referring to FIG. 2, bayonet fitting B is shown withdrawn from handle H. Handle H is illustrated at broken lines 22 with the outline of the toothpick T receiving cavity. Bayonet fitting 16 can be observed.

With respect to bayonet fitting 16 it will be noted that the bayonet fitting is provided with a toothpick of previously described design; i.e., the actual toothpick is made from semi-rigid plastic of sufficient narrowness with a blunted tip to allow for complete access into the gingival sulcuf in addition to the interproximal areas; incremental colored markings every two (2) millimeters giving the user exact information on depth of penetration in the subgingival areas; 90° right angle bendability for proper access.

Mounting of the toothpick can be made as desired for permitting the bend. For example, the toothpick can be made of a conformable material accommodating the bend illustrated at 26. Alternately, the toothpick can be mounted to a detent mechanism between separated portions of the bayonet fitting 16.

Regarding the incremental colored markings, the reader will understand that dental patients sometimes have oral cavities (periodontal pockets) adjacent the dentition that must be cleaned. Often the user cannot conveniently sense or see the depth of penetration of a cleaning toothpick appliance. Consequently, I provide the markings M on the toothpick as a reference. Typically, the user can look at the incremental colored markings, judge the effective depth of penetration, and effect cleaning. (See FIGS. 3 and 7)

Although the design of the device is to have the bayonet fitting and its compatible case/handle to be made in plastic and ultimately discardable, and alternate design for the product is to have the handle/case component and the bayonet made in metal and have the plastic toothpick only, along with a housing hub, replaceable when it has worn out.

The reader will understand that this device can be sold with toothpick T already mounted thereto. Alternatively, the device can be vended with the slot already disposed in bayonet fitting 16. The user may thereafter from time to time refresh the reusable toothpick utilized.

Referring to FIG. 3, mounting of the toothpick T to the handle H is illustrated. Specifically, bayonet fitting B has been reversed. Bayonet mounting 14 has been inserted interior to handle H. In this insertion, toothpick T protrudes from the handle.

It will be seen that handle H and bayonet fitting B are approximately three times as long as toothpick T.

Further, and viewing FIG. 4, it will be seen that bayonet B is given an overall elliptical section. Likewise, handle H is similarly given an elliptical configuration. This cross section enables the toothpick to be conveniently handled.

Referring to FIG. 5, use of the toothpick is shown from the disposition of FIG. 3 on the front teeth. Specifically, it will be noticed that handle H with bayonet fitting B placed therein fits conveniently between the thumb and forefingers. Manipulation of toothpick T occurs with leverage of the full hand. Required accuracy of manipulation can be achieved. The handle H provides suitable resistance to enable firm retention of the exposed toothpick in the hand.

Further, the overall toothpick and handle are of an extended length. Thus the user can open his mouth and clean not only the posterior interpoximal spaces. but the posterior subgingival areas as well.

The reader will appreciate that due to the design features of the toothpick (narrowness, semi-blunted, semi-rigid, 90° bendability and incremental markings) not only are the interproximal areas of the dentition easily accessible, but the critical subgingival areas as well.

Referring to FIG. 6 a toothpick T' is illustrated with respect to the handle in an end-on view looking down the handle similar to the view of FIG. 4. Here however it can be seen toothpick T' has an elliptical cross section as it protrudes from and extends without the bayonet B and the handle H (underlying bayonet B).

It will be remembered that bayonet B and the attached handle H are flattened in a plane. It can also be seen that due to the elliptical cross section of the toothpick T' the toothpick can bend in a direction that is within the plane of the handle.

The importance of the bendability within the plane of the handle can best be understood with respect to FIG. 7.

Referring to FIG. 7, the use of this article can be understood. Handle H is shown gripped at the flattened side between two digits, these digits being shown in phantom.

If the reader will extend the digits to the vicinity of the mouth, he will understand that the thumb and forefinger come together easily defining a substantially vertical interface the skin. This is especially true when the hands are maneuvered in the vicinity of the mouth with the arms being held in a natural position adjacent the side to the torso. It can be seen that handle H is conveniently gripped between the digits in a manner that will easily permit vertical angular manipulation of the handle.

It may now be understood how the toothpick T' bends. Specifically, it bends in the plane of the flattened handle. That is to say that when the handle is manipulated with its flattened side extending substantially vertically, the toothpick bends in a vertical plane parallel to the plane of the major axis of the elliptical cross section of the handle.

Stopping here, it will be seen that the toothpick T' extends outwardly and downwardly toward the molar M. The penetration of the pick is here into a periodontal pocket. The particular pocket is the gingival sulcuf adjacent a molar.

It will be noted that the toothpick T' is provided with markings as before. These provided markings enable the novice toothcleaner utilizing this device to penetrate a measured distance between the tooth and gums to effect cleaning.

I have found that an experienced user of this device can tactilely locate the required amount of penetration. Where however the user is unaccustomed to the device, the degrees of penetration are best checked visually.

In FIG. 7, we have omitted the gums of the user for convenience. It will be understood that the extension of my disclosed toothpick extends over the top of the gum to effect the desired cleaning. Thus is will be seen that my disclosed toothpick for the first time renders a sanitary encased toothpick capable of participating in a modern program of oral hygiene. This modern program of dental hygiene can include cleaning of periodontal pockets such as the gingival sulcuf of a molar. Prior art metal and wood toothpicks are unsuitable for this purpose. Specifically, they lack the required bendability and conformability. Furthermore, they are not designed for the disclosed cooperative manipulation between the handle of the pick and the periodontal pockets of the user which I have disclosed.

FIGS. 8-12 are perspective illustrations of the disclosed article in proper use for subgingival plaque removal in different areas of the mouth.

FIG. 8 illustrates the simplest way the pick can be used perpendicular to the long axis of the teeth in a horizontal manner so that the pick contacts surfaces of adjacent teeth simultaneously with the pick being situated between the interproximal tooth contact and the inter-dental papilla (the scalloped point of gum tissue between the teeth).

FIG. 9 illustrates the pick, not at a 90° angle to the teeth, but at 45°. The reader will realize the pick can be used anywhere from a 45° (as in FIG. 9) to almost 0° (if completely parallel to the long axis of the tooth.) The pick is not between two teeth, but is now under the gumline is into the gingival sulcus. The pick is least used on the outside surface of the tooth (facial) or the inside surface of the tooth (linqual), but is used most predominantly on the tooth surfaces between the teeth (and below the gumlines). There are two of these surfaces; one is the surface of the tooth that faces the front of the mouth (called the mesial), the other is the surface facing the back of the mouth (the distal). In the view of FIG. 9, the mesial aspect of the tooth (an upper right second bicuspid) is being accessed. This area is easier to access than the distal tooth surface because the pick can be kept straight during use.

FIG. 10 illustrates the pick being used to access the back side (distal) of the same tooth. Due to the location of this surface and the lack of access due to the limitations of the mouth and cheek, the pick must be bent to a right angle (and rotated clockwise) to penetrate subgingivally and de-plaque this area.

FIG. 11 is a perspective down the axis of the handle H, but this area (distal) aspect of the upper left first molar being approached from the lingual—or palatal—direction, represents the ultimate challenge for subgingival plaque control—definitely a difficult area to both see and reach. With practice, it can readily be done in a tactile manner.

FIG. 12 illustrates accessing of the distal surface (from the facial aspect) of a lower right first molar.

The reader will understand from the view of FIGS. 8-12, that the particular flexibility and length ratios of the handle to the pick enable the unique access for dental hygiene, especially subgingival, provided by the disclosed pick.

What is claimed is:

1. A toothpick handle with a mounted toothpick for the removal of plaque and food and debris from both the interproximal and subgingival areas of the human dentition comprising in combination:
    a hollow handle defining a cavity and having an essentially elliptical cross-section defining major and minor axes, said handle having two opposing flattened sides extending essentially parallel to the major axis of the handle for gripping in the digits of the human hands;
    a toothpick formed of bendable plastic material attached to and protruding from the handle, said toothpick having an essentially elliptical cross-section defining major and major axes, the major axis of the toothpick being substantially longer than the minor axis of the toothpick, the major axis of said toothpick being disposed normally to the flattened sides of said handle whereby said toothpick can be bent within the plane of said handle while said handle is gripped between digits of the human hand;
    wherein said toothpick is attachable to the handle in a first position where the toothpick protrudes into the cavity of the handle, and a second reversed position where the toothpick protrudes outwardly from the handle.

2. The invention of claim 1 and wherein said toothpick is mounted to a fitting, said fitting having first and second mounts;
    said first mount being configured for receiving said toothpick;
    said hollow cavity being sufficient to receive said toothpick;
    said handle configured to receive both said first and second mounts whereby in the first position, the first mount is received by said handle so that the toothpick is received within the handle for safe and sanitary transport and in the second and reversed position, the second mount is received by said handle so that said toothpick is exposed away from said handle for manipulation by the user.

3. The invention of claim 2, wherein said toothpick is bendable at least about 90° in the area where the toothpick is received by the fitting.

4. The invention of claim 1 and comprising and including markings along the length of said toothpick whereby a user can judge the degree of subgingival penetration of said toothpick within a periodontal pocket of the mouth.

* * * * *